(12) United States Patent
Beilfuss

(10) Patent No.: US 9,078,937 B2
(45) Date of Patent: Jul. 14, 2015

(54) REFRIGERATOR APPLIANCE AND METHOD FOR USE WITH FRAGRANCE DISPENSER

(71) Applicant: General Electric Company, Schenectady, NY (US)

(72) Inventor: Robert Charles Beilfuss, Fisherville, KY (US)

(73) Assignee: General Electric Company, Schanectady, NY (US)

(*) Notice: Subject to any disclaimer, the term of this patent is extended or adjusted under 35 U.S.C. 154(b) by 145 days.

(21) Appl. No.: 14/057,560

(22) Filed: Oct. 18, 2013

(65) Prior Publication Data

US 2015/0108669 A1  Apr. 23, 2015

(51) Int. Cl.
*A61L 9/12* (2006.01)
*B01F 3/04* (2006.01)
*F25D 3/00* (2006.01)

(52) U.S. Cl.
CPC ... *A61L 9/12* (2013.01); *B01F 3/04* (2013.01); *F25D 3/00* (2013.01)

(58) Field of Classification Search
CPC ................ A61L 9/12; B01F 3/04; F25D 3/00
USPC ............. 261/30, DIG. 88; 222/129.1; 62/389, 62/440
See application file for complete search history.

(56) References Cited

U.S. PATENT DOCUMENTS 8,596,087 B2 * 12/2013 Park ............................... 62/389
2007/0145074 A1  6/2007 Sevcik

* cited by examiner

*Primary Examiner* — Robert A Hopkins
(74) *Attorney, Agent, or Firm* — Dority & Manning, P.A.

(57) ABSTRACT

Refrigerator appliances for use with fragrance dispensers, and methods for operating refrigerator appliances, are provided. A method includes providing a fragrance dispenser in a housing, the housing disposed in a dispenser recess defined in the refrigerator appliance. The method further includes flowing a gas from an outlet conduit into the fragrance dispenser.

20 Claims, 3 Drawing Sheets

REFRIGERATOR APPLIANCE AND METHOD FOR USE WITH FRAGRANCE DISPENSER

FIELD OF THE INVENTION

The present subject matter relates generally to refrigerator appliances, and more particularly for methods and apparatus for single serve dispenser use in refrigerator appliances.

BACKGROUND OF THE INVENTION

Certain refrigerator appliances include a dispenser for directing ice from the refrigerator's ice maker and/or liquid water to the dispenser. A user can activate the dispenser to direct a flow of ice or liquid water into a cup or other container positioned within the dispenser. Liquid water directed to the dispenser is generally chilled or at an ambient temperature.

Further, certain refrigerator appliances can also include features for dispensing heated liquid water. The heated liquid water can be used to make certain beverages, such as coffee or tea. Refrigerators equipped to dispense heated liquid water can assist with making such beverages. In some cases, however, users may desire only, for example, a single serving of a beverage, such as a hot beverage. Further, in some cases, users may desire a better smelling area near the refrigerator appliance.

Accordingly, a refrigerator appliance which included features for dispensing fragrances would be desired. In particular, methods and apparatus for dispensing fragrances from refrigerator appliances would be advantageous.

BRIEF DESCRIPTION OF THE INVENTION

In accordance with one embodiment of the present disclosure, a method for operating a refrigerator appliance is disclosed. The method includes providing a fragrance dispenser in a housing, the housing disposed in a dispenser recess defined in the refrigerator appliance. The method further includes flowing a gas from an outlet conduit into the fragrance dispenser.

In accordance with another embodiment of the present disclosure, a method for operating a refrigerator appliance is disclosed. The method includes providing a single serve dispenser in a housing, the housing disposed in a dispenser recess defined in the refrigerator appliance. The method further includes flowing a liquid from an outlet conduit into the single serve dispenser, and flowing a gas from the outlet conduit into the single serve dispenser after flowing the liquid. The method further includes providing a fragrance dispenser in the housing, and flowing a gas from the outlet conduit into the fragrance dispenser.

In accordance with another embodiment of the present disclosure, a refrigerator appliance for use with a fragrance dispenser is disclosed. The refrigerator appliance includes a cabinet defining a chilled chamber for receiving food or beverage items for storage, the cabinet defining an opening for accessing the chilled chamber, and a door mounted to the cabinet at the opening of the cabinet, the door defining a dispenser recess. The refrigerator appliance further includes a dispensing assembly. The dispensing assembly includes an outlet conduit configured for flowing a gas therefrom, the outlet conduit disposed in the dispenser recess, and a housing for supporting the fragrance dispenser, the housing disposed in the dispenser recess.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Figure 1:
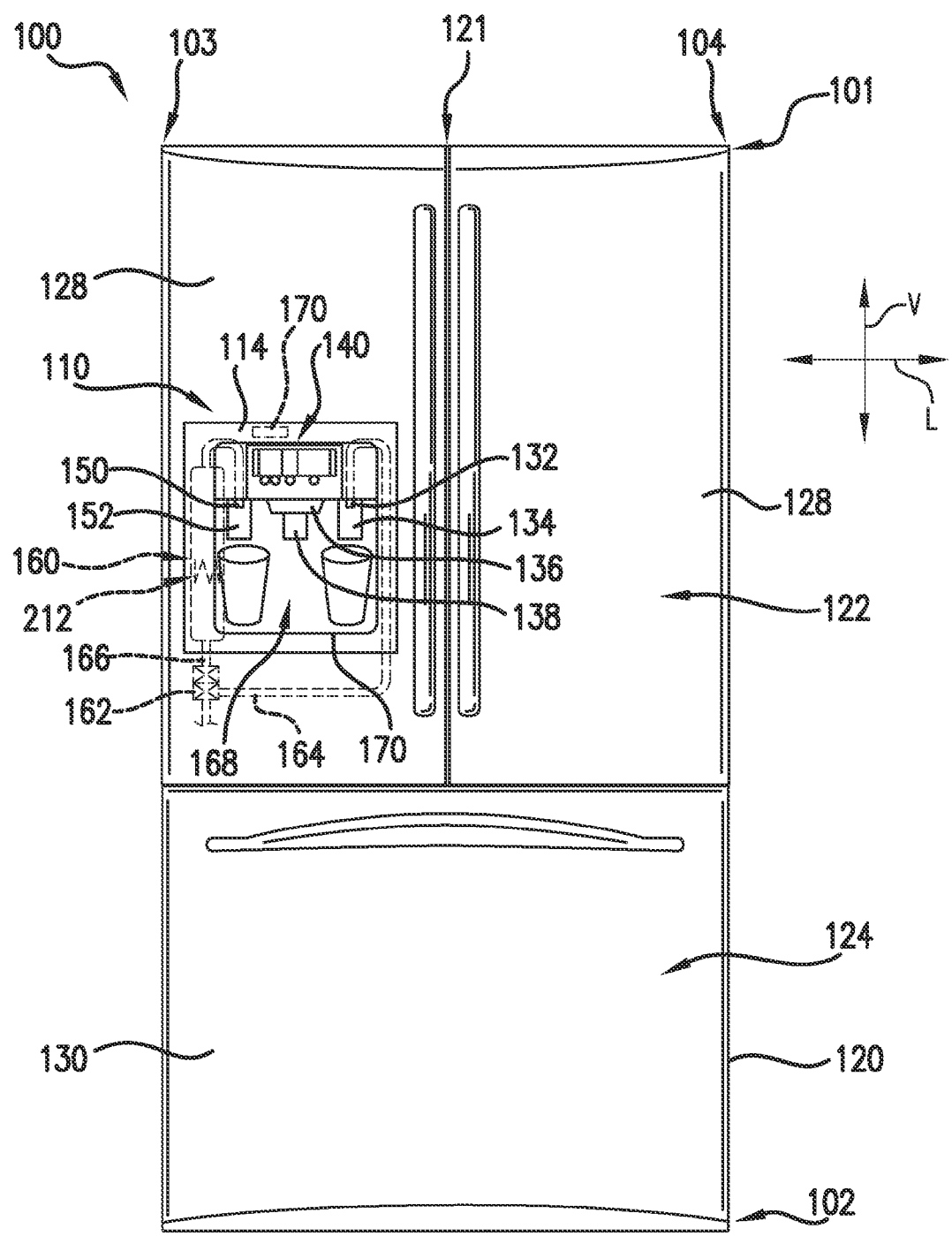
FIG. 1 provides a front, elevation view of an exemplary refrigerator as may be used with the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIG. 1 provides a front, elevation view of a refrigerator appliance 100 according to an exemplary embodiment of the present subject matter. Refrigerator appliance 100 includes a cabinet or housing 120. Housing 120 extends between an upper portion 101 and a lower portion 102 along a vertical direction V and also extends between a first side portion 103 and a second side portion 104 along a lateral direction L. A transverse direction T (see FIGS. 3-6) may additionally be defined perpendicular to the vertical direction and lateral direction L. Housing 120 defines chilled chambers, e.g., a fresh food compartment 122 positioned adjacent upper portion 101 of housing 120 and a freezer compartment 124 arranged at lower portion 102 of housing 120. Housing 120 also defines a mechanical compartment (not shown) for receipt of a sealed cooling system for cooling fresh food compartment 122 and freezer compartment 124.

Refrigerator appliance 100 is generally referred to as a bottom mount refrigerator appliance. However, it should be understood that refrigerator appliance 100 is provided by way of example only. Thus, the present subject matter is not limited to refrigerator appliance 100 and may be utilized in any suitable refrigerator appliance. For example, one of skill in the art will understand that the present subject matter may be used with side-by-side style refrigerator appliances or top mount refrigerator appliances as well.

Refrigerator doors 128 are rotatably hinged housing 120, e.g., at an opening 121 that permits access to fresh food compartment 122, in order to permit selective access to fresh food compartment 122. A freezer door 130 is arranged below refrigerator doors 128 for accessing freezer compartment 124. Freezer door 130 is mounted to a freezer drawer (not shown) slidably coupled within freezer compartment 124.

Refrigerator appliance 100 may also include a dispensing assembly 110 for dispensing various fluids, such as liquid water and/or ice to a dispenser recess 168 defined on one of refrigerator doors 128. Dispensing assembly 110 includes a dispenser 114 positioned on an exterior portion of refrigerator appliance 100. Dispenser 114 includes several outlets for accessing ice, chilled liquid water, and heated liquid water. As will be understood by those skilled in the art, liquid water from a water source, such as a well or municipal water system, can contain additional substances or matter. Thus, as used herein, the term "water" includes purified water and solutions or mixtures containing water and, e.g., elements (such as calcium, chlorine, and fluorine), salts, bacteria, nitrates, organics, flavor additives and other chemical compounds or substances.

To access ice, chilled liquid water, and heated liquid water, water-dispensing assembly 110 may for example include a chilled water paddle 134 mounted below a chilled water outlet 132 for accessing chilled liquid water and a heated water paddle 152 mounted below a heated water outlet 150 for accessing heated liquid water. Similarly, an ice paddle 138 is mounted below an ice outlet 136 for accessing ice. As an example, a user can urge a vessel such as a cup against any of chilled water paddle 134, heated water paddle 152, and/or ice paddle 138 to initiate a flow of chilled liquid water, heated liquid water, and/or ice into the vessel within dispenser recess 168, respectively.

A control panel or user interface panel 140 may be provided for controlling the mode of operation of dispenser 114, e.g., for selecting crushed or whole ice. In additional exemplary embodiments, refrigerator appliance 100 may include a single outlet and paddle rather than three separate paddles and dispensers. In such embodiments, user interface panel 140 can include a chilled water dispensing button (not labeled), an ice-dispensing button (not labeled), a heated water dispensing button (not labeled), and a steam-dispensing button (not labeled) for selecting between chilled liquid water, ice, heated liquid water, and steam, respectively.

Outlets 132, 136, and 150 and paddles 134, 138, and 152 may be an external part of dispenser 114, and are positioned at or adjacent dispenser recess 168, e.g., a concave portion defined in an outside surface of refrigerator door 128. Dispenser 114 is positioned at a predetermined elevation convenient for a user to access ice or liquid water, e.g., enabling the user to access ice without the need to bend-over and without the need to access freezer compartment 124. In the exemplary embodiment, dispenser 114 is positioned at a level that approximates the chest level of a user.

Refrigerator appliance 100 may also include features for generating heated liquid water and/or steam and directing such heated liquid water and/or steam to dispenser recess 168. Thus, refrigerator appliance 100 need not be connected to a residential hot water heating system in order to supply heated liquid water and/or steam to dispenser recess 168. In particular, refrigerator appliance 100 includes a water heating assembly 160 mounted within refrigerator door 128 for heating water therein. Refrigerator appliance 100 may include a tee-joint 162 for splitting a flow of water. Tee-joint 162 directs water to both a heated water conduit 166 and a chilled water conduit 164.

Heated water conduit 166 is in fluid communication with water heating assembly 160 and heated water outlet 150. Thus, water from tee-joint 162 can pass through water heating assembly 160 and exit refrigerator appliance 100 at heated water outlet 150 as heated liquid water or steam. Conversely, chilled water conduit 164 is in fluid communication with chilled water outlet 132. Thus, water from tee-joint 162 can exit refrigerator appliance 100 as chilled liquid water at chilled water outlet 132. In alternative exemplary embodiments, chilled water conduit 164 and heated water conduit 166 are joined such that chilled and heated water conduits 164 and 166 are connected in parallel or in series to each other and dispense fluid at dispenser recess 168 from a common outlet.

Operation of the refrigerator appliance 100 can be regulated by a controller 170 that is operatively coupled to user interface panel 138 and/or various sensors as discussed below. User interface panel 138 provides selections for user manipulation of the operation of refrigerator appliance 100 such as e.g., selections between whole or crushed ice, chilled water, and/or other various options. In response to user manipulation of the user interface panel 138 or sensor signals, controller 170 may operate various components of the refrigerator appliance 100. Controller 170 may include a memory and one or more microprocessors, CPUs or the like, such as general or special purpose microprocessors operable to execute programming instructions or micro-control code associated with operation of refrigerator appliance 100. The memory may represent random access memory such as DRAM, or read only memory such as ROM or FLASH. In one embodiment, the processor executes programming instructions stored in memory. The memory may be a separate component from the processor or may be included onboard within the processor. Alternatively, controller 170 may be constructed without using a microprocessor, e.g., using a combination of discrete analog and/or digital logic circuitry (such as switches, amplifiers, integrators, comparators, flip-flops, AND gates, and the like) to perform control functionality instead of relying upon software.

Controller 170 may be positioned in a variety of locations throughout refrigerator appliance 100. In the illustrated embodiment, controller 170 is located within the user interface panel 138. In other embodiments, the controller 170 may be positioned at any suitable location within refrigerator appliance 100, such as for example within a fresh food chamber, a freezer door, etc. Input/output ("I/O") signals may be routed between controller 170 and various operational components of refrigerator appliance 100. For example, user interface panel 138 may be in communication with controller 170 via one or more signal lines or shared communication busses.

Figure 2:
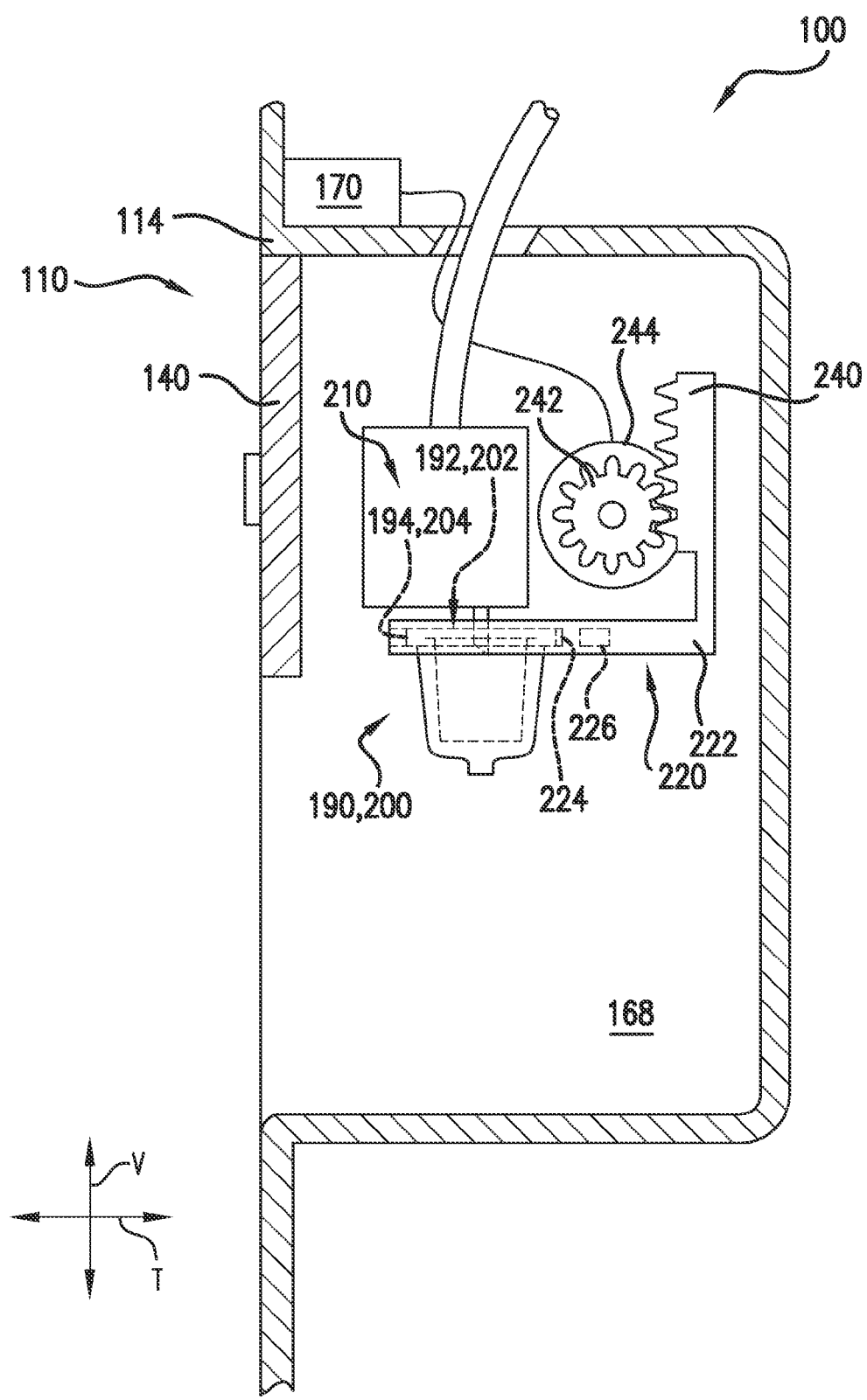
FIG. 2 illustrates a dispensing assembly of a refrigerator apparatus according to one embodiment of the present disclosure.

Referring now to FIG. 2, one embodiment of a dispensing assembly 110 is illustrated. As discussed above, apparatus for dispensing fragrances, as well as single serve beverages, from refrigerator appliances 100 are desired. Accordingly, the present disclosure is further directed to such apparatus.

As discussed herein, refrigerator appliance 100 may be utilized with single serve dispensers 200 and fragrance dispensers 190. A single serve dispenser 200 is generally a container which contains a predetermined amount of a substance to be mixed with a suitable liquid, such as water, etc. For example, coffee, tea, chocolate, or other suitable consumable or non-consumable substances may be contained within the dispenser 200. A top cover 202 may enclose an opening of the container, and may be puncturable and/or removable to access the substance therein. For example, in some embodiments, the top cover 202 may be formed from a suitable foil material, such as aluminum foil. Dispenser 200 may additionally include a lip 204, which may facilitate placing the dispenser in a housing, as discussed below, such as by sliding the dispenser into the housing. A liquid may then be introduced into the dispenser 200, and the liquid and substance may then flow from the dispenser 200 into, for example, a container (not shown) typically placed below the dispenser 200.

A fragrance dispenser 190 is generally a container which contains a predetermined amount of a substance to be mixed with a suitable gas, such as air. For example, potpourri, gaseous or liquid based fragrances such as colognes or perfumes, or other suitable non-consumable substances may be contained within the dispenser 190. A top cover 192 may enclose an opening of the container, and may be puncturable and/or removable to access the substance therein. For example, in some embodiments, the top cover 192 may be formed from a suitable foil material, such as aluminum foil. Dispenser 190 may additionally include a lip 194, which may facilitate placing the dispenser in a housing, as discussed below, such as by sliding the dispenser into the housing. A gas may then be introduced into the dispenser 190, and the gas and substance may then flow from the dispenser 190, typically to be dispersed into the environment outside of the refrigerator appliance 100.

As shown, a dispensing assembly 110 may include an outlet conduit 210. The outlet conduit 210 may be configured for flowing a fluid therefrom, such as liquid and/or gas. In some embodiments, for example, outlet conduit 210 may be a portion of heated water conduit 166, such as heated water outlet 150, or a portion of chilled water conduit 164, such as chilled water outlet 132. Alternatively, the outlet conduit 210 may be independent from such conduits. The outlet conduit 210 may generally be disposed in the dispenser recess 168, as illustrated.

In exemplary embodiments, the outlet conduit 210 may flow a gas, such as air, therethrough. For example, as discussed herein, air or another suitable gas can pass through a pump and valve to outlet conduit 210, and can then be flowed from outlet conduit 210.

Additionally, the outlet conduit 210 may flow a heated liquid, such as heated water, therethrough. For example, as discussed above, water can pass through a water heating assembly 160 and be heated therein, such that it flows from outlet conduit 210 as heated liquid water or steam. Thus, dispensing assembly 110 may include a heating element 212, which may for example, be disposed in water heating assembly 160 as illustrated, for heating the fluid before the fluid is flowed from the outlet conduit 210.

As further illustrated, a housing 220 may be provided for supporting the single serve dispenser 200 and fragrance dispenser 190. The housing 220 may also be disposed in the dispenser recess 168, as shown. The housing 220 may, for example, include a platform 222 which defines a recess 224 therein, into which a single serve dispenser 200 or fragrance dispenser 210 may be placed. For example, the lip 194, 204 of a dispenser 190, 200 may be slid into the recess 224, and the remainder of the dispenser 190, 200 may generally hang from the platform 222. In some embodiments, various sidewalls may additionally be included in the housing 220, and may extend from the platform 222 to surround the dispenser 190, 200 on various sides.

Additionally, in some embodiments, user interface panel 140 may further define the dispenser recess 168. As shown, panel 140 may for example extend from the dispenser 114, such as in the generally vertical direction V, such that a portion of the recess 168 is defined behind the panel 140. Additionally, panel 140 may serve to hide various other components, such as the outlet conduit 210, housing 220, and/or various components thereof in various positions as discussed herein. For example, from a point-of-view in the transverse direction T, a user may view the panel 140 but not be able to see such components hidden behind the panel 140 when in various positions, as discussed herein.

In some embodiments, one or both of the outlet conduit 210 and housing 220 according to the present disclosure are movable. Specifically, as shown, one or both of the outlet conduit 210 and housing 220 may be movable along a direction towards (and conversely away from) the other of the outlet conduit 210 and housing 220. Such movement in exemplary embodiments may along the generally vertical direction V. Such movement may facilitate use of the fragrance dispenser 190 and single serve dispenser 200, by allowing the dispenser 190, 200 to be loaded in the housing 220 and then provided with fluid from the outlet conduit 210. For example, such movement may bring the outlet conduit 210 and dispenser 190, 200 in contact, such that for example the outlet conduit 210 may puncture or otherwise penetrate the top cover 192, 202. Fluid may then be flowed from the outlet conduit 210 into the dispenser 190, 200 as required.

FIG. 2 illustrates one embodiment of the present disclosure, wherein the housing 220 is movable. As shown, housing 220 in these embodiments may include a rack 240, and a mating pinion gear 242 mounted to a motor 244 which in turn is in communication with the controller 170 may be provided. Operation of the motor 244 via commands from the controller 170 may move the housing 220 as desired. In alternative embodiments, the outlet conduit 210 or both the housing 220 and outlet conduit 210 may be movable. It should be understood that the present disclosure is not limited to such rack-and-pinion embodiments, and rather that any suitable mechanical apparatus may be utilized to facilitate movement of the housing 220 and/or outlet conduit 210.

Controller 170 may be in communication with one or both of the outlet conduit 210 and housing 220, and may be operable to move the one or both of the outlet conduit 210 and housing 220 as desired, such as along the generally vertical direction. For example, in some embodiments, the controller 170 may be operable to cause such movement based on a user input, such as via a user interacting with user interface panel 140. Additionally or alternatively, the controller 170 may be automatically operable based on sensing of a dispenser 190, 200 supported on the housing 220. A sensor 226 may be provided for sensing whether a dispenser 190, 200 is disposed in the housing 220. Sensor 226 may in some embodiments as shown be included in outlet conduit 210 or housing 220. One or both of the outlet conduit 210 and housing may be initially moved away from each other, to for example allow for loading of a dispenser 190, 200 in the housing 220. When a dispenser 190, 200 is placed in the housing 220, for example, the sensor 226 may detect the presence of the dispenser 190, 200 and communicate this to the controller 170, which may instruct one or both of the outlet conduit 210 and housing 220 to move towards each other, to for example bring the outlet conduit 210 and dispenser 190, 200 in contact. Further, when the outlet conduit 210 has for example completed the fluid flow therethrough into the dispenser 190, 200, the controller 170, sensor 226 or another suitable sensor (such as a sensor connected to the outlet conduit 210) may detect such completion. This may be communicated to the controller 170 and/or the controller 170 may instruct one or both of the outlet conduit 210 and housing 220 to move away from other, to for example allow for removal of the dispenser 190, 200 from the housing 220. When a dispenser 190, 200 is removed from the housing 220, for example, the sensor 226 may detect the absence of the dispenser 190, 200 and communicate this to the controller 170, which may instruct one or both of the outlet conduit 210 and housing 220 to move towards each other, to for example retract the outlet conduit 210 and/or housing 220 such that they are, for example, not visible. Alternatively, such various movements may be performed due to a user selecting various user inputs on the user interface panel 140.

It should be understood that the various movements of the various components as discussed herein may be performed based on user input and/or performed automatically. For example, all steps may be performed via user input, or automatically, or through a combination of user inputs and automatic steps. In one exemplary embodiment, for example, a user input facilitates an initial movement before or after a dispenser 190, 200 is placed on a housing 220 and the remaining movements are performed automatically.

Figure 3:
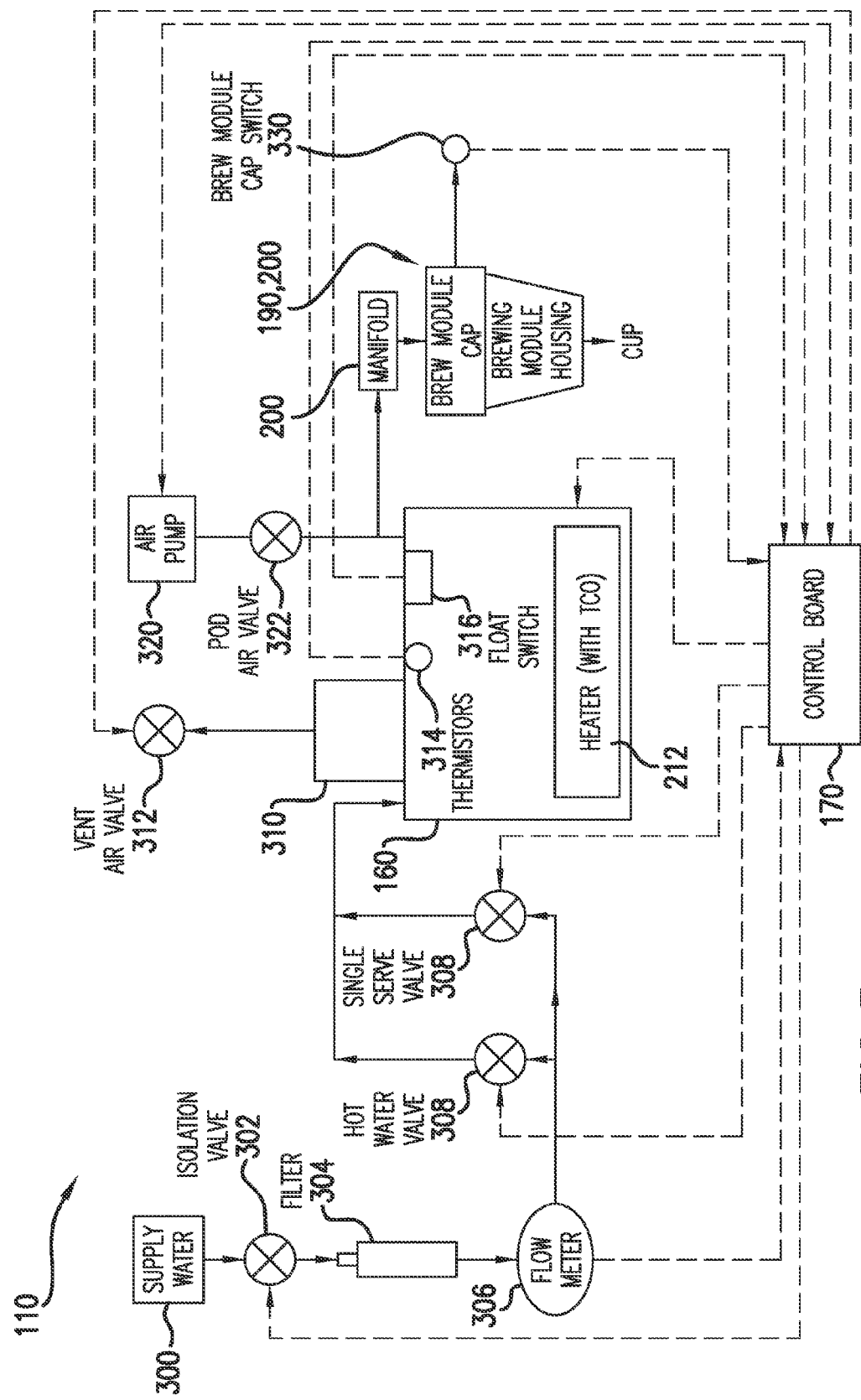
FIG. 3 illustrates a schematic view of a dispensing assembly according to one embodiment of the present disclosure.

FIG. 3 is a schematic illustration of one embodiment of various components of dispensing assembly 110. As discussed, dispensing assembly 110 may include an outlet conduit 210 through which gas and/or liquid flows into dispenser 190, 200. Various additional components may be provided to facilitate the flow of gas and/or liquid into and through the outlet conduit 210. Such components may variously be disposed in, for example, the dispenser 114, a door 128, 130, or another suitable location in the refrigerator appliance 100.

As shown, liquid may initially be supplied from a liquid source 300 through valve 302, such as an isolation valve, to a filter 304. The liquid may be filtered in the filter 304, and then flowed through a flow meter 306. One or more valves 308 may then control flow of the liquid to a containment chamber, such as water heating assembly 160. An expansion chamber 310 may be coupled to the containment chamber to, for example, allow gas generated due to liquid heating in the containment chamber to expand into the expansion chamber 310. A vent valve 312 may allow such gas to escape from the expansion chamber 310. Containment chamber may additionally include, for example, a thermistor 314 and a float switch 316, which may govern the level and supply of liquid.

Further, a gas pump 320 may be provided. The gas pump 320 may supply gas from a suitable gas source, such as the environment when air is utilized, to the dispensing assembly. A gas valve 322 may allow such gas to be provided to the outlet conduit 210.

Gas and liquid may thus be provided to outlet conduit 210 via the various other components of dispensing assembly 110. Thus, such various components, such as gas pump 320 and gas valve 322 with regard to the gas supply, may be connected to the outlet conduit 310 as shown. For example, gas may be supplied through pump 320 and valve 322. Liquid may be supplied from the containment chamber. Switches 330 which may for example be mounted on housing 220, and/or sensors 226 may be activated by dispensers 190, 200 to indicate that a supply of liquid or gas is required.

As illustrated controller 170 may be in communication with the various components of dispensing assembly 110, and may control operation of the various components. For example, the various valves, switches, etc. may be actuatable based on commands from the controller 170. As discussed, interface panel 140 may additionally be in communication with the controller 170. Thus, the various operations may occur based on user input or automatically through controller 170 instruction.

The present disclosure is further directed to methods for operating refrigerator appliances 100. A method may include, for example, providing a fragrance dispenser 190 in a housing 220, the housing 220 disposed in a dispenser recess 168 defined in the refrigerator appliance 100, as discussed herein. The method may further include flowing a gas, such as air, from an outlet conduit 210 into the fragrance dispenser 190, as discussed herein.

Such flowing step may include, for example, actuating a gas pump 320 to flow the gas to the outlet conduit 210, as discussed herein. Additionally, such flowing step may include actuating an air valve 322 to allow the gas to flow to the outlet conduit 210, as discussed herein.

Further, in some embodiments, a method may include moving one of the housing 220 or the outlet conduit 210 such that the outlet conduit 210 contacts the fragrance dispenser 190, as discussed herein.

Methods according to the present disclosure may further include various steps for providing liquids. For example, a method may include providing a single serve dispenser 200 in a housing 220, the housing 220 disposed in a dispenser recess 168 defined in the refrigerator appliance 100, as discussed herein. A method may further include flowing a liquid from an outlet conduit 210 into the single serve dispenser 200.

In some embodiments, such method according to the present disclosure may further include flowing a gas from the outlet conduit 210 into the single serve dispenser 200 after flowing the liquid. By flowing gas after the flow of liquid and into a single serve dispenser 200, excess liquid may be cleared from the single serve dispenser 200 before removal thereof from the housing 220.

In exemplary embodiments, such various steps, in particular the actuation of the gas pump 320 and the air valve 322, may be performed independently of actuation of any liquid flow. Thus, for example, the steps of providing the fragrance dispenser 190 and flowing the gas from the outlet conduit 210 into the fragrance dispenser 190 may be performed independently of providing the single serve dispenser 200, flowing the liquid, and optionally flowing the gas from the outlet conduit 210 into the single serve dispenser 200. In other words, operation to flow a gas into a fragrance dispenser 190 may be an independent operation from any operation to flow a liquid into a single serve dispenser 200. A user input to begin gas operation may be separate from, and may not commence before or after, a liquid operation, and outlet conduit 210 may be configured for flowing gas therefrom independently of flowing liquid therefrom. Alternatively, however, such gas operation may follow such liquid operation. For example, after liquid operation, and upon removal of a single serve dispenser 200 and providing a fragrance dispenser 190, gas operation may automatically commence.

In some embodiments, various steps, such as the flowing steps, may be performed based on a user input. In these embodiments, a user may be required to interact with the user interface panel 140 to select such steps to be performed. Additionally or alternatively, various steps, such as the flowing steps, may be performed automatically. For example, each respective flowing step may be performed automatically after the respective providing step.

As discussed above, it should be understood that the various steps as discussed herein may be performed based on user input and/or performed automatically. For example, all steps may be performed via user input, or automatically, or through a combination of user inputs and automatic steps.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for operating a refrigerator appliance, the method comprising:
   providing a fragrance dispenser in a housing, the housing disposed in a dispenser recess defined in the refrigerator appliance; and
   flowing a gas from an outlet conduit into the fragrance dispenser.

2. The method of claim 1, wherein the flowing step comprises actuating a gas pump to flow the gas to the outlet conduit.

3. The method of claim 2, wherein the flowing step further comprises actuating an air valve to allow the gas to flow to the outlet conduit.

4. The method of claim 3, wherein the gas pump and the air valve are actuated independently of actuation of a liquid flow.

5. The method of claim 1, wherein the gas is air.

6. The method of claim 1, wherein the flowing step is performed based on a user input.

7. The method of claim 1, wherein the flowing step is performed automatically after the providing step.

8. The method of claim 1, further comprising moving one of the housing or the outlet conduit such that the outlet conduit contacts the fragrance dispenser.

9. A method for operating a refrigerator appliance, the method comprising:
   providing a single serve dispenser in a housing, the housing disposed in a dispenser recess defined in the refrigerator appliance;
   flowing a liquid from an outlet conduit into the single serve dispenser;
   flowing a gas from the outlet conduit into the single serve dispenser after flowing the liquid;
   providing a fragrance dispenser in the housing; and
   flowing a gas from the outlet conduit into the fragrance dispenser.

10. The method of claim 9, wherein the flowing step comprises actuating a gas pump to flow the gas to the outlet conduit.

11. The method of claim 10, wherein the flowing step further comprises actuating an air valve to allow the gas to flow to the outlet conduit.

12. The method of claim 9, wherein the steps of providing the fragrance dispenser and flowing the gas from the outlet conduit into the fragrance dispenser are performed independently of providing the single serve dispenser, flowing the liquid, and flowing the gas from the outlet conduit into the single serve dispenser.

13. The method of claim 9, wherein the gas is air.

14. The method of claim 9, wherein the step of flowing the gas from the outlet conduit into the fragrance dispenser is performed based on a user input.

15. The method of claim 9, wherein the step of flowing the gas from the outlet conduit into the fragrance dispenser is performed automatically after providing the fragrance dispenser in the housing.

16. The method of claim 9, further comprising moving one of the housing or the outlet conduit such that the outlet conduit contacts the fragrance dispenser.

17. A refrigerator appliance for use with a fragrance dispenser, comprising:
   a cabinet defining a chilled chamber for receiving food or beverage items for storage, the cabinet defining an opening for accessing the chilled chamber;
   a door mounted to the cabinet at the opening of the cabinet, the door defining a dispenser recess; and
   a dispensing assembly, the dispensing assembly comprising:
      an outlet conduit configured for flowing a gas therefrom, the outlet conduit disposed in the dispenser recess; and
      a housing for supporting the fragrance dispenser, the housing disposed in the dispenser recess.

18. The refrigerator appliance of claim 17, wherein the outlet conduit is configured for flowing the gas therefrom independently of flowing a liquid therefrom.

19. The refrigerator appliance of claim 17, wherein the dispensing assembly further comprises a gas pump and a gas valve, the gas pump and gas valve connected to the outlet conduit.

20. The refrigerator appliance of claim 17, wherein one of the outlet conduit and the housing is movable along a direction towards the other of the outlet conduit and the housing.

* * * * *